United States Patent [19]

Ash

[11] 4,368,737
[45] Jan. 18, 1983

[54] IMPLANTABLE CATHETER

[75] Inventor: Stephen R. Ash, Lafayette, Ind.

[73] Assignee: Purdue Research Foundation, West Lafayette, Ind.

[21] Appl. No.: 166,578

[22] Filed: Jul. 7, 1980

[51] Int. Cl.³ .............................................. A61M 25/00
[52] U.S. Cl. ..................................... 604/175; 604/283
[58] Field of Search ............... 128/213 A, 214 R, 348, 128/350 R, 245, 349; 222/103; 252/359

[56] References Cited

U.S. PATENT DOCUMENTS

| | | | |
|---|---|---|---|
| 504,424 | 9/1893 | De Pezzer | 128/349 R |
| 2,340,068 | 1/1944 | Limbert | 128/349 R |
| 2,431,587 | 11/1947 | Schnee | 128/348 |
| 3,481,338 | 12/1969 | Sobel et al. | 128/348 |
| 3,546,129 | 12/1970 | Berg et al. | 252/359 |
| 4,214,593 | 7/1980 | Imbruce et al. | 128/348 |
| 4,217,664 | 8/1980 | Faso | 128/348 |
| 4,266,999 | 5/1981 | Baier | 128/348 |
| 4,306,566 | 12/1981 | Sinko | 128/348 |

FOREIGN PATENT DOCUMENTS 2541919 3/1977 Fed. Rep. of Germany ... 128/350 R

Primary Examiner—V. Millin
Attorney, Agent, or Firm—John R. Nesbitt; Robert E. Harris

[57] ABSTRACT

An implantable catheter is disclosed that is particularly useful as a peritoneal access device. The catheter includes an elongated, flexible tube, one portion of which is adapted to extend into the body of a user with a second portion external to the body of the user. The end of the one portion of the tube within the body has connected thereto a flexible terminating member comprised of a pair of spaced apart sheets extending outwardly of the periphery of the tube in a direction substantially normal to the axis of the end portion of the tube with the spaced sheets forming a passage therebetween communicating with the interior of the tube through a central opening in one of the sheets so that access to the tube is through the passage formed by the spaced sheets. In the disclosed embodiments, the sheets are either substantially flat discs held in spaced relationship with respect to one another by means of a plurality of columns extending between the discs or are apertured, curved sheets with opposite edges connected together. Columns of reduced diameter are also disclosed to enable folding of the discs to facilitate insertion into the body of a user.

19 Claims, 15 Drawing Figures

IMPLANTABLE CATHETER

FIELD OF THE INVENTION

This invention relates to an implantable catheter and, more particularly, relates to a catheter useful as a peritoneal access device.

BACKGROUND OF THE INVENTION

It is often times necessary and/or desirable to utilize a catheter positioned within the body of a user, or patient, to drain a fluid from the body. Such a catheter might be needed, for example, to drain a body cavity such as the chest, bladder, or peritoneum.

Although hemodialysis is now the major method of support of end-stage renal disease patients in the United States, peritoneal dialysis has recently been utilized to a greater extent. This is due, at least in part, to peritoneal dialysis being relatively simple, painless, and not causing severe intradialytic symptoms. In addition, patient toleration of this type of dialysis has been found to be good even in the presence of systemic diseases besides renal failure.

While peritoneal dialysis was found to have numerous advantages, problems still remain, however, that are peculiar to this type of dialysis, including a requirement for large volumes of sterile fluid, the occurrence of infection, and particularly subcutaneous infections (due at least in part to catheter migration), the length of time required for treatment, and/or impedence or blockage of the outflow from the catheter.

The development of the silicone peritoneal catheter has allowed chronic peritoneal dialysis to become feasible. One of the best of such silicone catheters included a long subcutaneous tract and a curved intra-peritoneal portion, but problems still remained, including the occurrence of infection which proved to be a severe limitation. With the later addition of dacron cuffs, which cuffs prompted tissue in-growth, the occurrence of infections was greatly decreased.

In addition, while this type of catheter proved to function well during inflow, outflow, which is almost always slower than inflow, was found to be often inadequate and complete outflow obstruction was found to sometimes occur. This so-called "one-way" catheter obstruction may be due to upward dislodgement of the catheter, wrapping of the catheter by omentum, or constipation. In addition, the tendency to outflow obstruction was also found to be worsened by high flow rates in the peritoneal catheter.

To minimize the problems of omental obstruction of catheter drain holes, various modification has heretofore been suggested, including "stand-off" devices to hold the bowels away from the catheter (such as through the use of a balloon near the intra-abdominal end of the catheter, through the use of thin silicone rubber sheets in a position perpendicular to the intra-abdominal portion of the catheter and/or through the use of a catheter with a disc having a large plurality of small holes over the entire surface).

Even with modifications heretofore proposed and/or devised, problems of slow outflow and/or of one-way obstruction of peritoneal catheters still remained and improvements still were needed to affect, for example, a minimization of omentum involvement of the catheter, prevention of bowel obstruction of the catheter, and/or decrease of fluid inlet velocity to the catheter.

With respect to prior art patents, U.S. Pat. Nos. 3,818,511 and 3,707,967 show a catheter which can be implanted in a patient, while U.S. Pat. Nos. 4,160,454; 3,698,396; 3,520,298; and 3,064,653 relate to peritoneal catheters. In addition, the problem of catheter tip migration is discussed in U.S. Pat. No. 3,540,451.

SUMMARY OF THE INVENTION

This invention provides an improved catheter that is particularly well suited for use as a peritoneal access device. In particular, the improved catheter of this invention provides advantages in terms of minimizing blockage of fluid flow through the catheter, including minimizing omentum involvement of the catheter and/or preventing obstruction of the catheter by bowels and the like, decreasing the fluid inlet velocity into the catheter, and/or anchoring of the catheter when implanted.

It is therefore an object of this invention to provide an improved catheter suitable for implanting in a patient.

It is another object of this invention to provide an improved catheter for use in draing a body cavity of a patient.

It is still another object of this invention to provide an improved implantable catheter that is particularly useful as a peritoneal access device.

It is yet another object of this invention to provide an improved implantable catheter that minimizes blockage of fluid flow through the catheter.

It is still another object of this invention to provide an improved catheter that minimizes omentum involvement of the catheter and/or prevent, bowel obstruction to fluid flow through the catheter.

It is yet another object of this invention to provide an improved implantable catheter that enables the fluid inlet velocity to the catheter to be decreased.

It is still another object of this invention to provide an improved implantable catheter that can be immobilized against the abdominal wall to optimally drain fluid from a patient.

With these and other objects in view, which will become apparent to one skilled in the art as the description proceeds, this invention resides in the novel construction, combination, and arrangement of parts substantially as hereinafter described and more particularly defined by the appended claims, it being understood that such changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and which.

DESCRIPTION OF THE INVENTION

Figure 1:
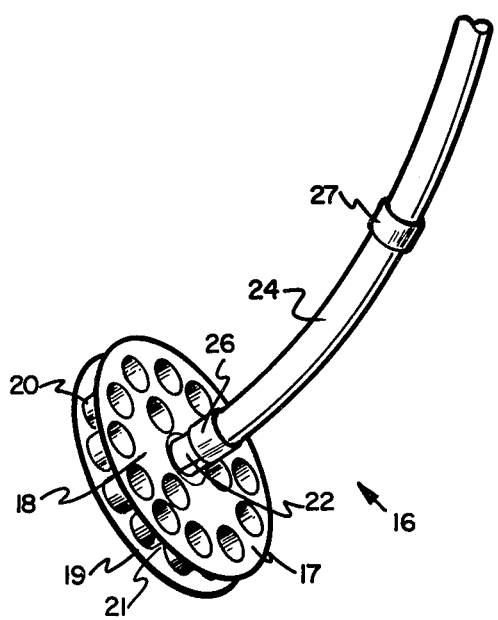
FIG. 1 is a perspective view of one embodiment of the implantable catheter of this invention.
Figure 2:
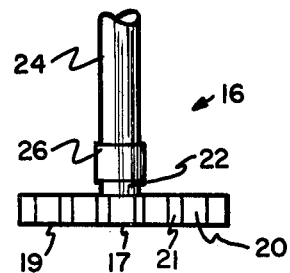
FIG. 2 is a side view of the catheter shown in FIG. 1.
Figure 3:
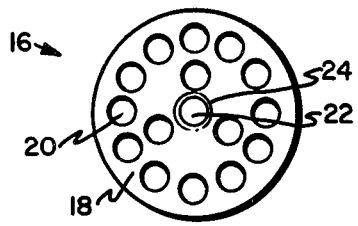
FIG. 3 is a top view of the catheter as shown in FIG. 1 with tube cut-away above the disc.

As shown in FIGS. 1 through 3, the implantable catheter 16 of this invention includes a terminating member 17 which consists of a pair of sheets or discs, 18 and 19, with the discs being maintained spaced by a plurality of columns, or pillars, 20, extending between the discs. By this arrangement, an opening, or passage, 21, is provided between the bi-layered discs, as shown in FIGS. 1 and 2. If desired, discs 18 and 19 can also be aperatured.

A central opening 22 is provided in disc 18. A tube 24 is connected with opening 22 so that the interior of the tube is in communication with the passage 21 formed by the spaced discs 18 and 19 to allow fluid flow therebetween. By this arrangement, fluid flow to tube 24 occurs into the end of the tube adjacent to the opening 22 in disc 18 only through the passage formed by the spaced discs to the interior of the catheter.

All the elements of terminating member 17 and tube 24 are formed of flexible material, and are preferably formed from silicone rubber. In a working embodiment of this invention, discs 18 and 19 were 0.01 inches in thickness and 1.75 inches in diameter, columns 20 were 0.25 inches in diameter and 1.25 inches in height, and tube 24 was 0.25 inches OD and 0.125 inches ID and of a length as desired (at least 6 inches or longer).

As also shown in FIG. 1, a pair of cuffs 26 and 27 (preferably Dacron velour cuffs about 0.625 inches in width) are wrapped about the outer periphery of tube 24 with cuff 26 being placed about 0.25 inches from the base of disc 18 and cuff 27 being placed about 4.5 inches from disc 18.

Figure 4:
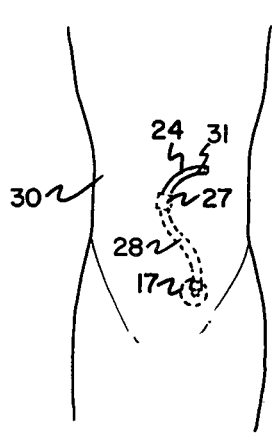
FIG. 4 is a front sketch view showing preferred placement of the catheter illustrated in FIGS. 1 through 3 in the peritoneal cavity of a user.
Figure 5:
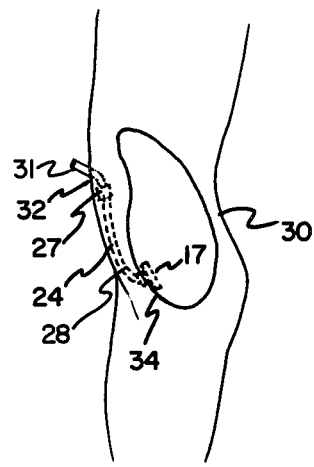
FIG. 5 is a side view showing preferred placement of the catheter illustrated in FIGS. 1 through 3 in the peritoneal cavity of a user.

The preferred placement of the disc catheter (as shown in FIGS. 1 through 3) in a body cavity (and in particular in the peritoneal cavity), is illustrated in FIGS. 4 and 5. As shown, the lower portion 28 of tube 24 and the adjacent terminating member 17 are inserted into the body cavity of a user, or patient, 30, with the upper, or outer, portion 31 of the tube 24 extending outside the body of the user through opening 32. As shown in FIG. 5, the lower portion 28 of tube 24 and terminating member 17 extend through the lower abdominal wall 34 so that terminating member 17 is thereafter preferably anchored, or immobilized, against the lower portion of the abdominal wall 34.

Figure 7:
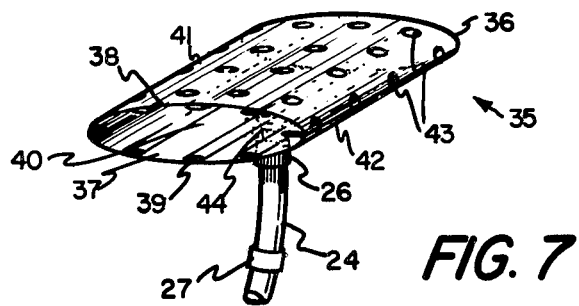
FIG. 7 is a perspective view of an alternate embodiment of the implantable catheter of this invention.

A second, or alternate, embodiment 35 of the implantable catheter is shown in FIG. 7. As shown, embodiment 36 is a T-tube catheter having terminating element 36 which consists of a pair of curved sheets 37 and 38 each of which sheets preferably have supporting ribs 39 extending therealong inside the passage 40 formed by the sheets and parallel to the opposite joined edges 41 and 42 of the sheets. Ribs 39 prevent collapse of the sheets during use (i.e., maintains the sheets in spaced relationship with respect to one another except at the joined edges). As shown in FIG. 7, the opposite edges 41 and 42 are preferably integral with one another so that sheets 37 and 38 form an oval tubular structure. A plurality of spaced aperatures 43 are provided throughout sheets 37 and 38.

Tube 24 is connected to a central opening 44 in sheet 37 in the same manner as discussed in connection with the embodiment of the disc catheter shown in FIGS. 1 through 3. In this manner, the interior of tube 24 is in communication with passage 40 formed between sheets 38 and 39 to allow fluid flow therebetween. Cuffs 26 and 27 are preferably utilized in the same manner as in the embodiment of the disc catheter shown in FIGS. 1 through 3.

In a working embodiment of the T-tube catheter shown in FIG. 7, silicone rubber sheets about 4 inches long and 0.5 inches wide with two millimeter high ribs were attached to a silicone rubber tube having a 0.25 inches OD and 0.125 inches ID.

The T-tube catheter shown in FIG. 7 may be implanted in the same manner as described in connection with the disc catheter shown in FIGS. 1 through 3 and as illustrated in FIGS. 4 and 5.

Figure 6:
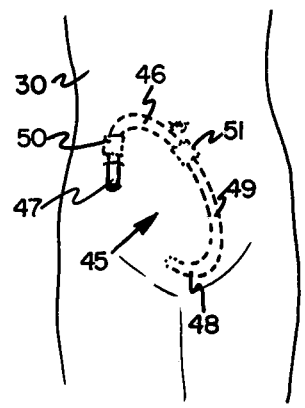
FIG. 6 is a front sketch view showing common placement, for reference purposes, of a prior art catheter in the peritoneal cavity of the user.

Placement of the catheter of this invention is similar to that of typical catheters now known and utilized known as the Tenckhoff catheter, which catheter and common placement is shown for reference purposes in FIG. 6. As shown, this reference catheter 45 includes a tube 46 the top portion 47 of which extends from the body 30 of the user and the bottom portion 48 of which is curved and includes a plurality of aperatures 49 therein. A pair of cuffs 50 and 51 are also preferably utilized.

Figure 8:
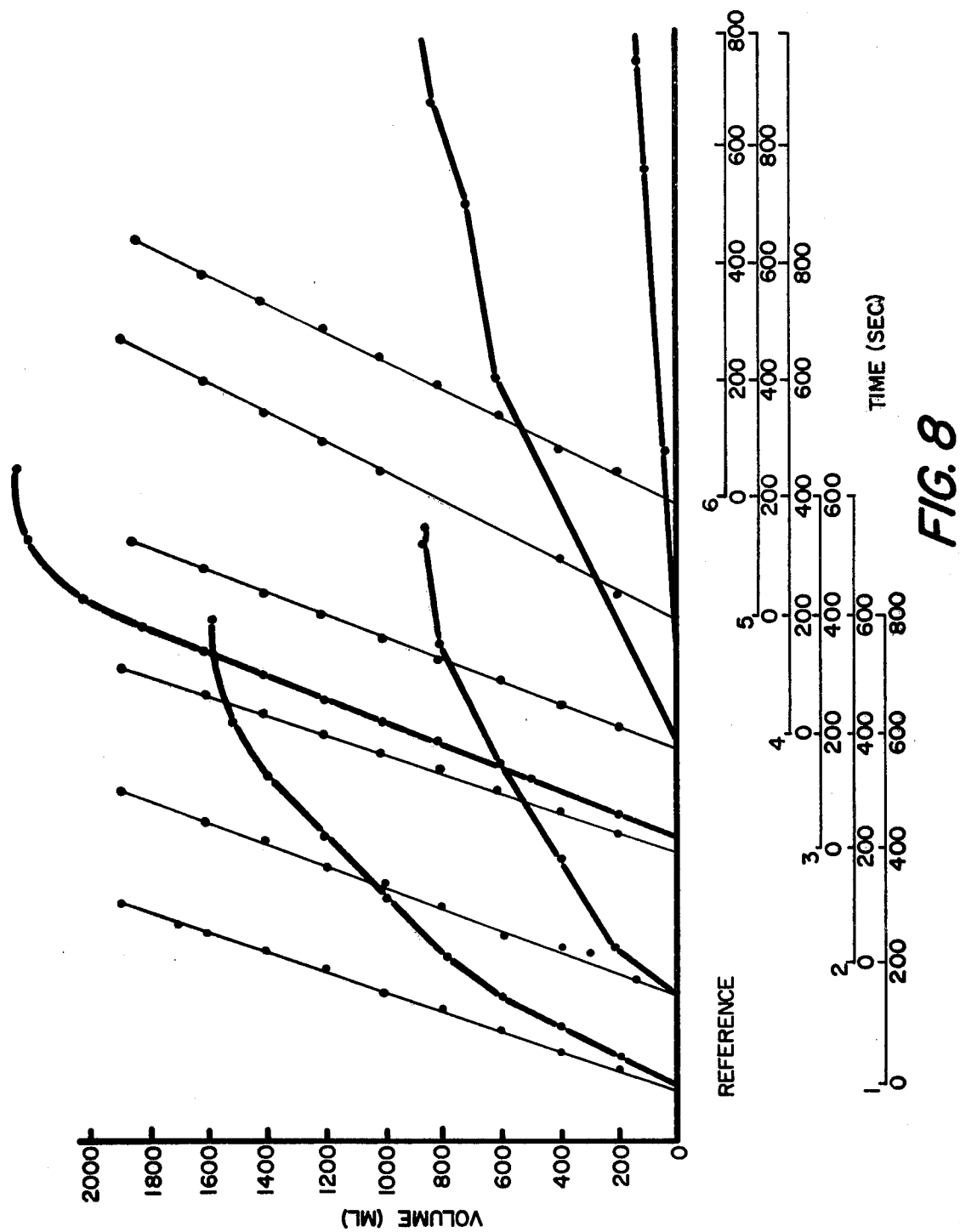
FIGS. 8 through 10 are graphs illustrating results for inflow and outflow versus time for catheters as shown in FIGS. 1, 7, and 6 (reference), respectively.

For reference purposes, the graph of FIG. 8 illustrates inflow and outflow volumes versus time for a reference catheter such as shown in FIG. 6 and placed in the abdomen of an animal (dog) for study purposes. As shown, the thin lines in FIG. 8 indicate inflow while the thickened lines indicate outflow for six tests as shown (no output was obtained from the sixth test). The six tests illustrated were performed in the first six days after catheter placement.

Figure 9:
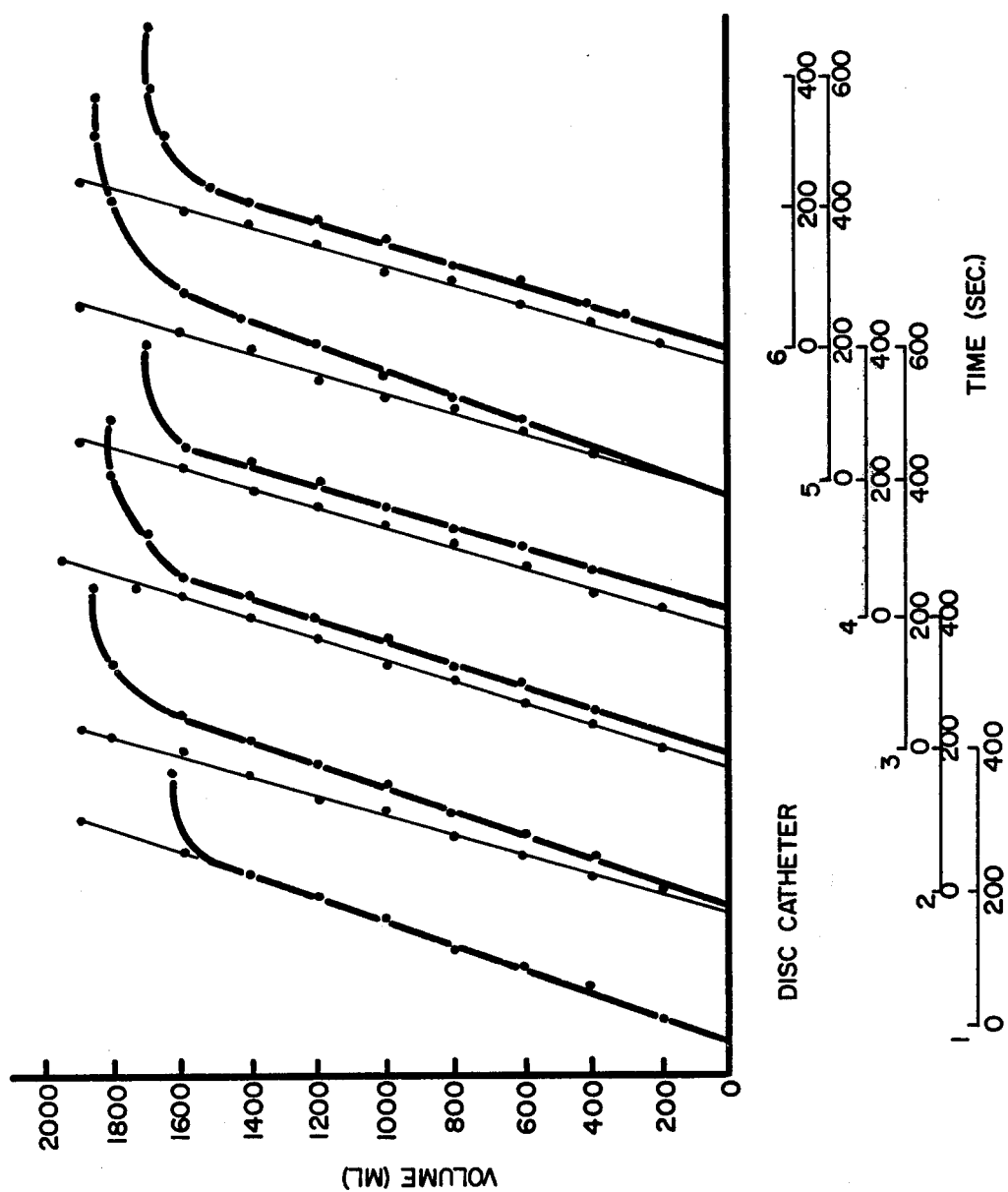

The graph of FIG. 9 illustrates inflow and outflow volumes versus time for the disc catheter (shown in FIGS. 1 through 3) placed in the abdomen of an animal (dog) for study purposes. Again, the thin lines indicate inflow while the thickened lines indicate outflow for the six tests as shown. The six tests illustrated were again performed in the first six days after placement. For this catheter, residual volume maximum was found to be 300 ml.

Figure 10:
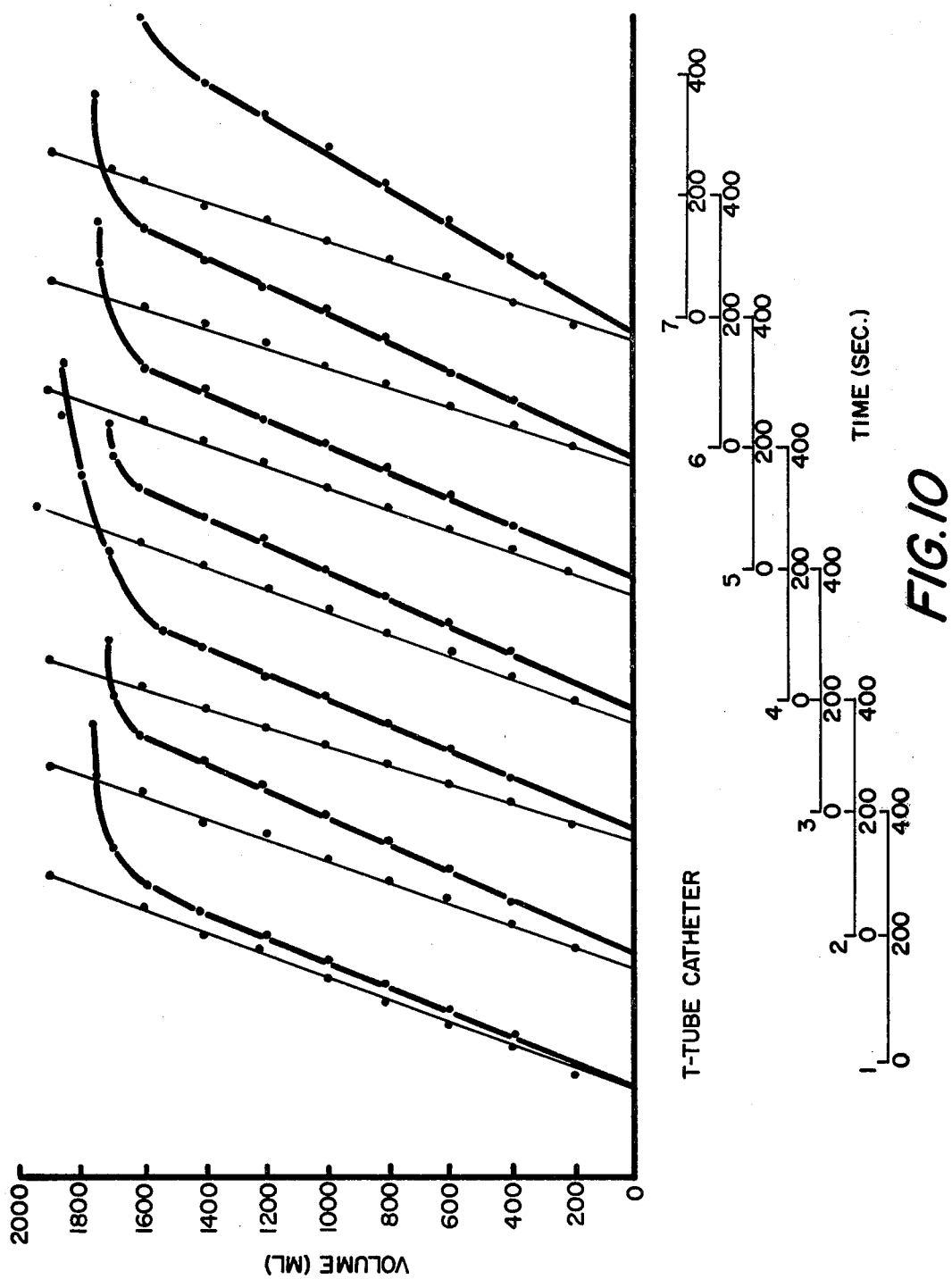

The graph of FIG. 10 illustrates inflow and outflow volumes versus time for the T-tube catheter (shown in FIG. 7) placed in the abdomen of an animal (dog) for study purposes. Again, the thin lines indicate inflow while the thickened lines indicate outflow for seven tests. The seven tests were performed on the first six days after catheter placement. For this catheter, residual volume in the abdomen was found to be 0 to 200 ml.

As can be appreciated from the graphs of FIGS. 8 through 10, the standard, or reference, catheter was found to have a variable flow and a residual volume. While the inflow was approximately the same, with a flow rate of 4.0 to 6.1 ml/sec during each of these six trials or tests, outflow was markedly variable, ranging from 0 ml/sec to 5.0 ml/sec during most of the outflow (FIG. 8). In addition, a residual volume of up to two liters was obtained (except for one test when more fluid was removed than was placed in the abdomen). The outflow characteristics were not markedly changed by manipulation of the abdomen. The results utilizing this catheter are thought to be consistent with results previously reported by others, and hence valid for reference or comparison purposes.

Disc catheter 16 exhibits improved outflow characteristics as shown by FIG. 9. Inflow was again relatively constant at 6.0 to 7.0 ml/sec, and outflow proceeded at almost the same flow rate, 5.3 to 6.7 ml/sec. In addition, a relatively constant residual was obtained of 0 to 300 cc, and catheter function was identical at the sixth test as it was on the first test. Manipulation of the abdomen was not performed during any of these trials.

T-tube catheter 36 also showed adequate drainage characteristics as shown by the graph of FIG. 10. Inflow was consistent at 5.4 to 6.8 ml/sec, while outflow was relatively consistent but decreased slightly from 5.1 to 3.6 ml/sec over the course of seven tests (FIG. 10). In addition, residual was similar to that of disc catheter 16 with 0 to 300 cc residual. Manipulation of the abdomen was not performed during any of these outflow tests.

For all three catheters (i.e., reference, disc, and T-tube), the red blood cell blood count rose initially to approximately 60,000/mm$^3$, but by the end of one week it was approximately 10,000/mm$^3$. It stayed less than 10,000/mm$^3$ for up to 20 days. White count was 20,000 to 60,000/mm$^3$ throughout all the catheter tests. The protein output of the peritoneal fluid was low at approximately 185 mm percent. Numerous gram stains were performed and no organisms were seen in the peritoneal fluid. Cultures were obtained and all of these were sterile. The animals were kept on ampicillin orally throughout the duration of the experiment. At removal, neither the T-tube nor the disc catheter had significant fibrous obstructions. There was some fibrous material attached, but this was easily rinsed free. The reference catheter had fibrous tissue including all holes except those most proximal to the catheter outer portion. The reference catheter was found to be embedded in several loops of bowel within the abdominal cavity, and there was some matting around the catheter.

Figure 11:
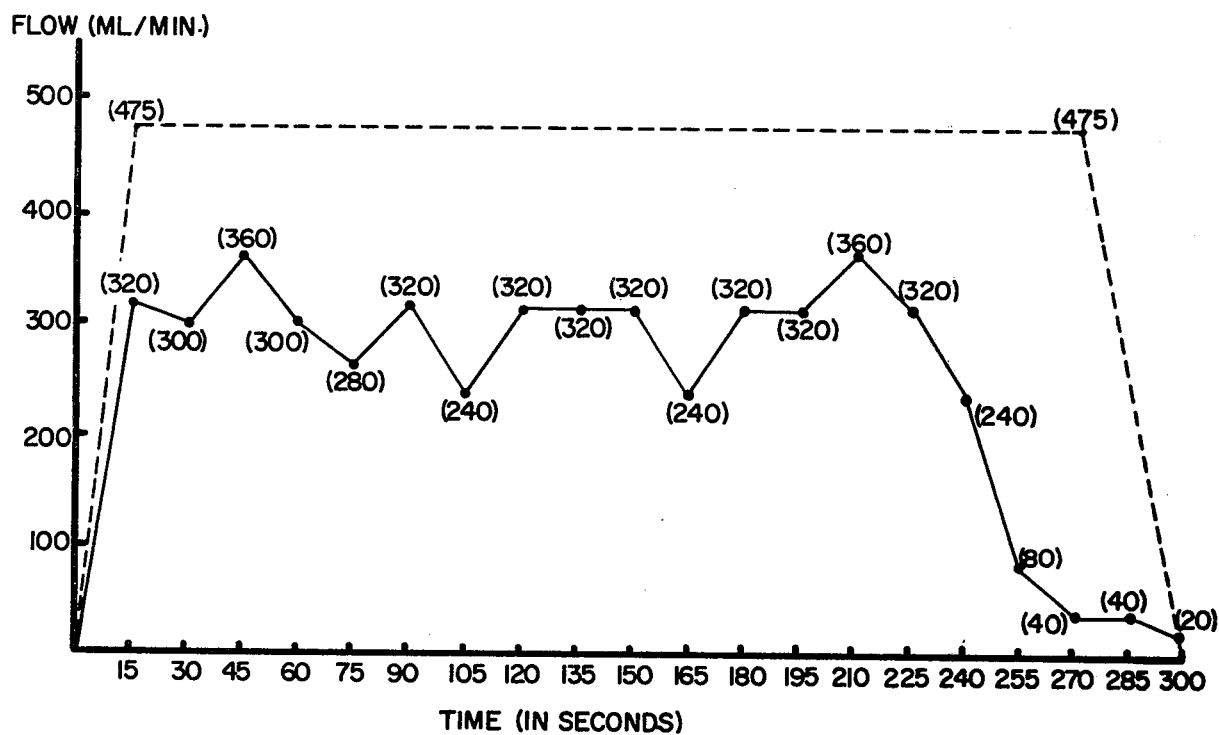
FIG. 11 is a graph illustrating the outflow rate of a catheter of this invention in a chronically uremic dog.

FIG. 11 illustrates the outflow rate of the catheter in a chronically uremic dog with the dotted line indicating in vitro flow tests with flow from a two liter container through standard tubing to a reservoir and the solid line indicating the in vitro outflow rate after two liters of fluid were placed in the abdomen. In each test shown in FIG. 11, hydrostatic pressure head equals 100 cm $H_2O$. The in vitro flow tests indicate flow through standard tubing into a reservoir was 475 ml/min. Outflow from the peritoneal cavity was slightly less, at approximately 320 ml/min over 225 sec. This in vivo fluid was obtained six weeks after onset of renal failure and catheter placement. At time of removal, the catheter had some fibrous overgrowth but had no definite obstruction of fibrous tissue and the subcutaneous tract showed no evidence of inflammation. The animal was kept on antibiotics (ampicillin orally) during the course of renal failure.

The measurement of intra-abdominal pressure showed a calculation of the pressure gradient between inflow and outflow to and from the abdomen. Utilizing this pressure gradient, resistances were calculated for inflow and outflow for the peritoneal catheters, and these resistances are set forth in Table 1. With the reference catheter, the resistance to outflow is shown in Table 1 to very markedly rise from 24 to 450 and finally to infinity. The disc catheter is shown in Table 1 to have a very stable inflow and outflow resistance, with the inflow ranging from 13 to 15 cm $H_2O$/ml/min and the outflow resistance 9.3 to 11 cm $H_2O$/ml/min. The T-tube catheter is shown in Table 1 to have a slightly decreasing inflow resistance from 17 to 13 cm $H_2O$/ml/min, then a slightly increasing outflow resistance on day six from 13 to 17 cm $H_2O$/ml/min. These resistances all allowed adequate drainage of the abdomen by approximately 400 seconds.

Figure 12:
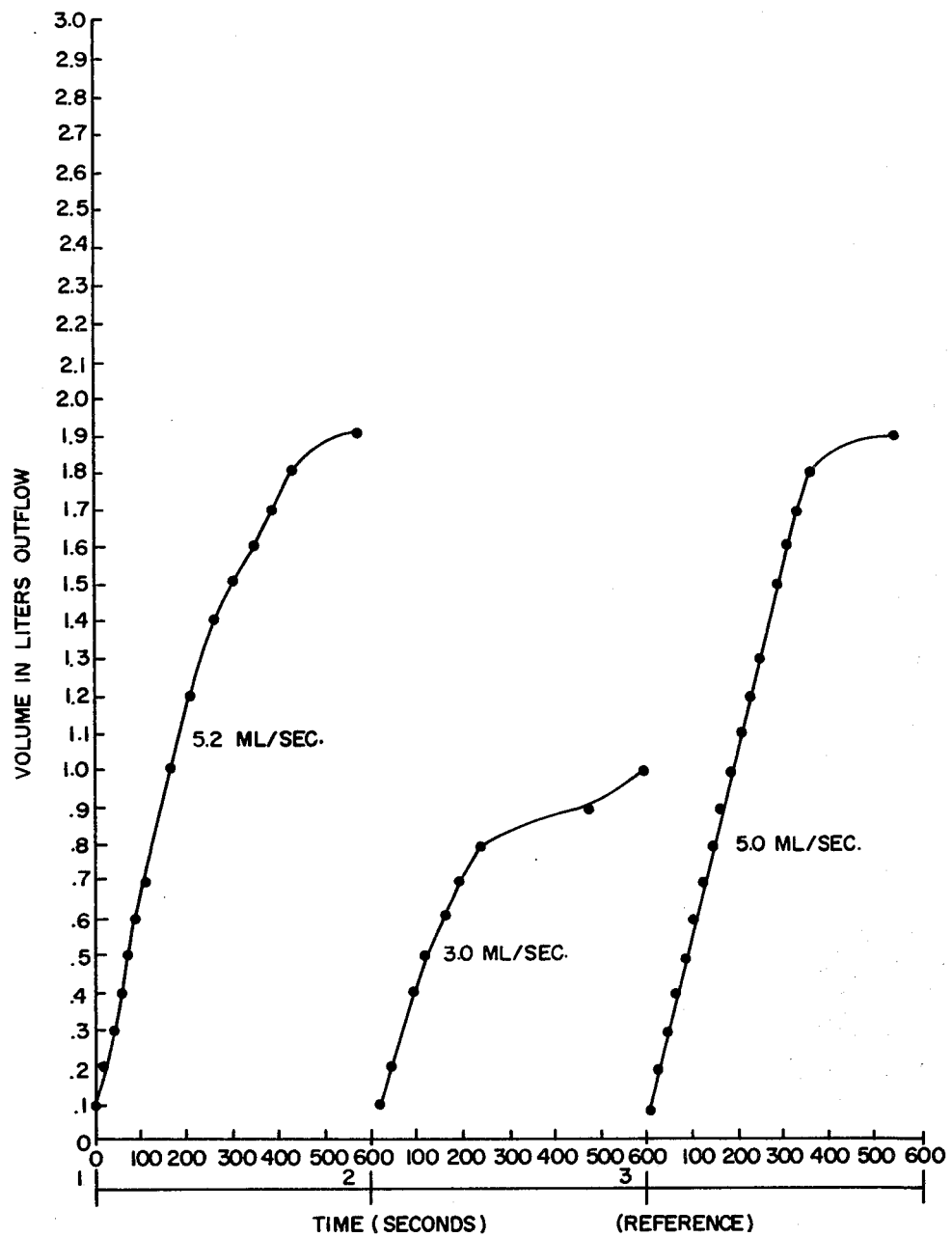
FIGS. 12 and 13 are graphs illustrating outflow volume versus time for a human patient with respect to a reference catheter (as shown in FIG. 6) and a disc catheter (as shown in FIGS. 1 through 3)

For comparison purposes to illustrate testing on a human, a human dialysis patient was studied with a reference catheter. With placement of the reference catheter as seen in FIG. 6 in the human patient, outflow volume versus time is shown in the graph in FIG. 12. The results, shown in FIG. 12 were delivered by electric scale and recordings were taken at three separate exchanges on three successive days. 1.5% dianeal was infused six hours before each of the represented outflows. As shown in FIG. 12, outflow rate varied from 3 to 5.2 ml/sec, and a high residual volume was occasionally obtained. Abdominal manipulation failed to increase outflow at these times. Slight patient discomfort was felt at maximal inflow rates and a resistor was applied to the inflow tubing during most of the exchanges.

For testing on a human patient, the disc catheter was placed as shown in FIGS. 4 and 5, and dialysis was conducted in the same manner as with the reference catheter, using a 1.5 to 2 liter exchanges.

TABLE 1

| Design | | Outflow-Inflow Total | 1 | 2 | 3 | 4 | 5 | 6 | 7 |
|---|---|---|---|---|---|---|---|---|---|
| Reference | Inflow | ml/min | 5.5 | 5.4 | 6.1 | 5.3 | 4.0 | 4.0 | |
| | Outflow | | 3.7/2.1 | 1.7/1.2 | 5.0 | 0.6 | 0.2 | 0 | |
| | $\Delta P_i$ | cm $H_2O$/ml/min | 90.5 | 90.5 | 90.5 | 90.5 | 90.5 | 90.5 | |
| | $\Delta P_o$ | | 60.1 | 60.1 | 60.1 | 60.1 | 60.1 | 60.1 | |
| | $R_i$ | cm $H_2O$/ml/min | 16 | 17 | 15 | 17 | 23 | 23 | |
| | $R_o$ | | 24/43 | 53/75 | 18 | 151 | 450 | ∞ | |
| Disc | Inflow | ml/min | 6.0 | 6.7 | 6.6 | 6.5 | 6.7 | 7.0 | |
| | Outflow | | 6.0 | 6.0 | 6.5 | 5.7 | 5.3 | 6.6 | |
| | $\Delta P_i$ | cm $H_2O$/ml/min | 90.5 | 90.5 | 90.5 | 90.5 | 90.5 | 90.5 | |
| | $\Delta P_o$ | | 60.1 | 60.1 | 60.1 | 60.1 | 60.1 | 60.1 | |
| | $R_i$ | cm $H_2O$/ml/min | 15 | 14 | 14 | 14 | 14 | 13 | |
| | $R_o$ | | 10 | 10 | 9.3 | 11 | 11 | 9.1 | |
| T-Tube | Inflow | ml/min | 5.4 | 6.0 | 6.6 | 5.8 | 6.3 | 6.6 | 6.8 |
| | Outflow | | 5.1 | 5.1 | 4.8 | 5.0 | 4.9 | 4.6 | 3.6 |
| | $\Delta P_i$ | cm $H_2O$/ml/min | 90.5 | 90.5 | 90.5 | 90.5 | 90.5 | 90.5 | 90.5 |

TABLE 1-continued

| Design | Outflow-Inflow Total | 1 | 2 | 3 | 4 | 5 | 6 | 7 |
|---|---|---|---|---|---|---|---|---|
| $P_o$ | | 60.1 | 60.1 | 60.1 | 60.1 | 60.1 | 60.1 | 60.1 |
| $R_i$ | cm H$_2$O/ml/min | 17 | 15 | 14 | 16 | 14 | 14 | 13 |
| $R_o$ | | 12 | 12 | 13 | 12 | 12 | 13 | 17 |

The peritoneal fluid became completely clear on the third exchange, and remained clear thereafter. Inflow and outflow tests were performed at two week time periods with the collecting bag placed 0.6 m below the catheter exit site, and the flow rate from the abdomen was reproducibly 5 ml/sec throughout the exchange. Outflow exceeded inflow volume for both 1.5% and 4.25% Dianeal. The entire outflow took seven minutes, and no discomfort was felt by the patient at the highest inflow rate obtainable (no inflow resistance).

Figure 13:
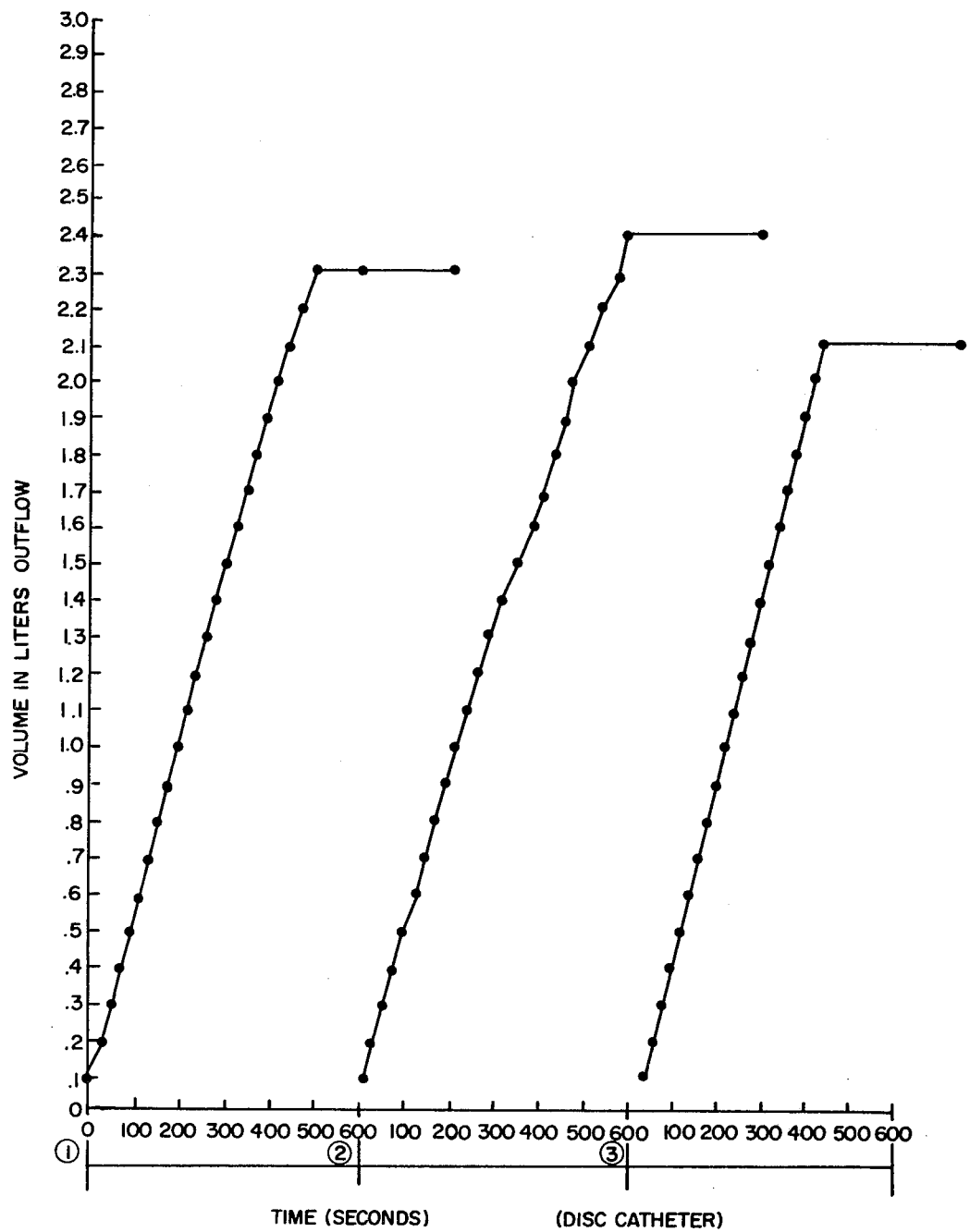

With respect to disc catheter 16 positioned as shown in FIGS. 4 and 5 in a human patient, outflow volume versus time is shown in the graph of FIG. 13. Again, values were determined by electric scale and readings were taken at three separate exchanges on three separate days. 1.5% Dianeal was infused six hours before each of the represented outflows.

Figure 14:
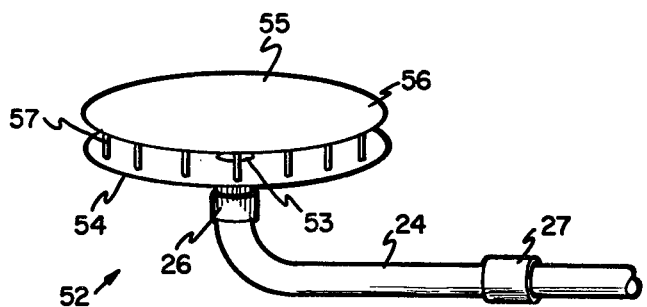
FIG. 14 is a perspective of a second alternate embodiment of the implantable catheter of this invention.

A third embodiment 52 of the invention is shown in FIG. 14. As shown, tube 24, having cuffs 26 and 27 thereon, is connected to the central opening 53 of disc 54 of the terminating element 55. Disc 54 is spaced from disc 56 and the spacing between the discs is maintained by columns 57. The disc catheter 52 shown in FIG. 14 may be identical to the disc catheter 16 shown in FIGS. 1 through 3 except that columns 57 are relatively small in diameter (compared to the diameter of columns 20 of disc catheter 16) to maintain a 0.25 inch spacing between the discs, and tube 24 is curved at a 90° angle commencing about ¼ in. below disc 54.

Curving of tube 24 in disc catheter 52 allows the tubing to naturally follow the subcutaneous space and not deflect against the skin. In addition, this curvature helps to prevent inward drift (into the abdomen) of the column disc portion. In addition, the small upright columns 57 can be deformed to allow the sheets (discs 54 and 56) to become opposed. In this design, the discs can be rolled around inflow-outflow tube 24, and thus be rolled into a cylinder (which may be, for example, only about one centimeter in diameter).

Figure 15:
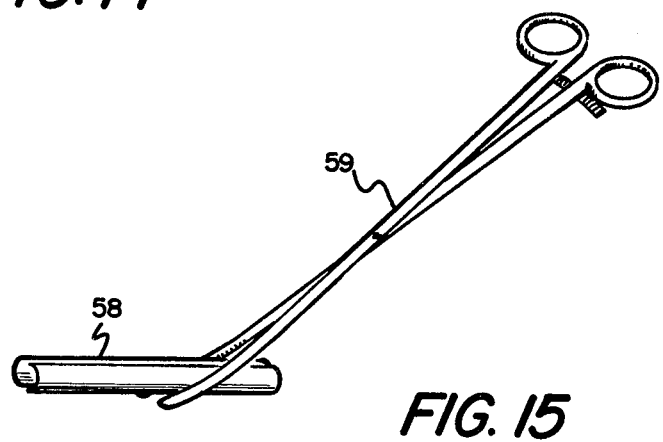
FIG. 15 is a perspective view of a clamping device for use in folding and inserting a folded catheter, as shown in FIG. 14 into a body cavity.

As shown in FIG. 15, a clamp with two stainless steel tubing halves 58 welded onto the arms of uterine packing forceps 59 may be utilized for insertion of disc catheter 52 when folded and rolled into a cylinder. Stainless steel halves 58 preferably have an inner diameter of one centimeter, and catheter 52, when rolled up, is thus easily placed on the inside of the two stainless steel halves 58. This clamp then allows placement through a one-centimeter incision in the peritoneum and allows release of the discs within the peritoneal cavity so that the terminating member 55 assumes its normal configuration as shown in FIG. 14.

As can be appreciated from the foregoing, the discs (or sheets) of the catheter of this invention are placed into the body cavity to be drained, and then retracted to lie against the proximal wall of the cavity where the thus implanted catheter is firmly held in place. This can be accomplished, for example, by making an incision through the abdominal wall and the adjoining portion of the peritoneum near the lower portion of the peritoneal cavity. The lower portion of tubing and the terminating member are then inserted through the incision and retracted until the terminating member is resting against the peritoneum. The peritoneum is then closed around the lower portion of tubing between the disc and lower cuff on the tube closest to the disc and this lower cuff is sutured to the abdominal wall. A tract is then formed under the skin of the abdominal wall from a location adjacent to the lower cuff to a point upwardly thereof, and on exit incision is made through the skin to this point. Tubing 24 is drawn through this tract and out through the incision with the upper cuff being sutured to the abdominal wall adjacent to the exit incision. Outflow of fluid enters the passage between the discs (or sheets) from the perimeter of the discs (or through apertures in the sheets) and flows to the central portion where it exits through central opening into the flexible tube, attached thereto. While the catheter of this invention is particularly useful for drainage of the peritoneum, other body cavities may also be drained, such as the chest or bladder, for example.

The catheter of this invention includes the following advantages:

1. A slow flow velocity occurs into the catheter because of the very large circumferential inlet port;
2. Because of the slow velocity, there is diminished irritation of the peritoneum or the adjacent surfaces during inflow;
3. There is decreased tendency for collapse of soft surfaces during outflow because of the decreased fluid flow velocity;
4. The step increase in size between the tube and terminating member of the catheter results in improved retention of the catheter within body cavities;
5. The placement of the terminating member of the catheter firmly against the wall of the body cavity prohibits the catheter from being completely enveloped by the bowels or other moveable parts of the body cavity; and
6. A smooth surface is presented to parts within the body cavity such as bowels, lungs, etc.

From the foregoing, it is to be appreciated that this invention provides an improved catheter that is particularly useful in peritoneal dialysis.

What is claimed is:

1. An implantable catheter for peritoneal access, said catheter comprising:

an elongated tubular member one portion of which is adapted to extend into the peritoneal cavity of the body of a user to an end within said cavity, and a second portion which is adapted to be external of the body of a said user; and a terminating member having first and second walls each of which is spaced with respect to the other at least at central and outer portions to thereby form a passage therebetween with said passage being maintained by reinforcing means engaging each of said first and second walls, said outer portions having access means for opening said passage externally of said catheter, and said central portion of said first wall having means defining an opening therein for engaging said end of said one portion of said tubular member so that said passage established between said first and second walls is in communication with the interior of said tubular member with said passage being substantially normal with respect to the axis of said end of said tubular member when said tubular member is in engagement with said means defining said opening in said first wall.

2. The catheter of claim 1 wherein said tubular member has at least one cuff thereon for preventing catheter infections.

3. The catheter of claim 1 wherein said tubular member and said terminating member are flexible.

4. The catheter of claim 3 wherein said flexible tubular and terminating members are made of silicone rubber.

5. The catheter of claim 1 wherein said pair of walls are thin, substantially flat sheets, and wherein said reinforcing means are colums extending between said sheets.

6. The catheter of claim 5 wherein said thin sheets are discs.

7. The catheter of claim 6 wherein said columns are spaced about the periphery of said discs.

8. The catheter of claim 5 wherein said columns are of sufficiently large diameter to define access means of small area relative to the area of said columns extending between said discs.

9. The catheter of claim 5 wherein said columns are of sufficiently small diameter to define access means of large area relative to the area of said columns extending between said discs.

10. The catheter of claim 1 wherein said pair of elements are curved sheets joined along opposite edges with said sheets having apertures therein.

11. The catheter of claim 10 wherein said reinforcing means extend along said sheets.

12. An implantable catheter for peritoneal access, said catheter comprising:
    an elongated, flexible tube one portion of which is adapted to extend through the abdominal wall and peritoneum of a user and having an end within the peritoneal cavity of said user when said one portion is positioned to extend through said abdominal wall and said peritoneum of user; and
    a terminating member including a pair of sustantially flat discs maintained in spaced relationship with respect to one another by a plurality of columns extending therebetween and engaging both of said discs, with one of said discs having an opening therein and being connected with said end of said elongated tube thereat so that the interior of said tube is in communication with the area between said discs whereby the interior of said tube is open through said end to the exterior of said catheter through said area between said discs.

13. The catheter of claim 12 wherein said discs extend outwardly from said tube in a direction substantially normal to the axis of the end of said tube.

14. The catheter of claim 13 wherein said discs extend for a distance outwardly from said tube a distance at least twice as far as that of the diameter of said tube.

15. The catheter of claim 12 wherein said columns are substantially equal in diameter to the diameter of said tube.

16. The catheter of claim 12 wherein said areas are much smaller in diameter than the diameter of said tube.

17. The catheter of claim 16 wherein said discs may be readily folded against said tube to facilitate insertion of said one end portion and terminating member through said abdominal wall and peritoneum of said user.

18. An improved catheter for peritoneal access, said catheter comprising:
    an elongated tube one portion of which is adapted to extend through the abodominal wall and peritoneum of a user and having an end within the peritoneal cavity of said user when said one portion is positioned to extend through said abdominal wall and said peritoneum of said user; and
    a terminating member including a pair of curved rectangular sheets joined along opposite edges to form a hollow area therebetween, said sheets having spaced apertures therein, with one of said sheets having an opening therein and being connected with said end of said elongated tube thereat so that said hollow area formed by said sheets is in communication with the interior of said tube whereby the interior of said tube is open to the exterior of said catheter through said hollow area, and each of said sheets having reinforcing means engaging said sheets.

19. The catheter of claim 18 wherein said reinforcing means are reinforcing rods extending along said sheets substantially parallel to said opposite edges of said sheets.

* * * * *